(12) United States Patent
Greaves

(10) Patent No.: US 8,075,638 B2
(45) Date of Patent: Dec. 13, 2011

(54) DICHROMOPHORE CARBONYL OR HETEROCYCLIC DYE, DYE COMPOSITION COMPRISING THIS DYE, PROCESS FOR DYEING KERATIN MATERIALS USING THIS DYE

(75) Inventor: Andrew Greaves, Magny-le-Hongre (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/679,657

(22) PCT Filed: Sep. 23, 2008

(86) PCT No.: PCT/EP2008/062711
§ 371 (c)(1),
(2), (4) Date: Sep. 27, 2010

(87) PCT Pub. No.: WO2009/040355
PCT Pub. Date: Apr. 2, 2009

(65) Prior Publication Data
US 2011/0023242 A1    Feb. 3, 2011

Related U.S. Application Data

(60) Provisional application No. 60/960,741, filed on Oct. 11, 2007.

(30) Foreign Application Priority Data

Sep. 24, 2007  (FR) ...................................... 07 57807

(51) Int. Cl.
*A61Q 5/10*  (2006.01)
*C07C 323/00*  (2006.01)

(52) U.S. Cl. ............. 8/405; 8/407; 8/435; 8/465; 8/642; 8/648; 562/426

(58) Field of Classification Search ............. 8/405, 407, 8/435, 465, 642, 648; 562/426
See application file for complete search history.

(56) References Cited

FOREIGN PATENT DOCUMENTS

| EP | 0 742 210 A1 | 11/1996 |
| EP | 0742 210 A1 * | 11/1996 |
| WO | WO 00/15723 | 3/2000 |
| WO | WO 2005/097051 A2 | 10/2005 |

OTHER PUBLICATIONS

STIC Search Report dated Feb. 25, 2011.*
H. Narkhede et al., "Fly-Ash-Supported Synthesis of 2-Mercaptobenzothiazole Derivatives under Microwave Irradiation," Synthetic Communications, vol. 37, pp. 573-577 (2007).
International Search Report for PCT/EP2008/062711, dated Dec. 21, 2009.

* cited by examiner

*Primary Examiner* — Eisa Elhilo
(74) *Attorney, Agent, or Firm* — Finnegan, Henderson, Farabow, Garrett & Dunner, LLP

(57) ABSTRACT

The invention relates to the dyeing of keratin materials using dichromophore dyes with a carbonyl or heterocyclic linker. The invention relates to a dye composition comprising a dye with a carbonyl or heterocyclic linker, and to a dyeing process with a lightening effect on keratin materials, in particular keratin fibers, especially human keratin fibers such as the hair, using said composition, optionally in the presence of a cosmetically acceptable acid or base. It similarly relates to novel dyes and to the uses thereof in lightening keratin materials. This composition makes it possible to obtain a coloring with a lightening effect which is particularly resistant and visible on dark keratin fibers.

17 Claims, No Drawings

DICHROMOPHORE CARBONYL OR HETEROCYCLIC DYE, DYE COMPOSITION COMPRISING THIS DYE, PROCESS FOR DYEING KERATIN MATERIALS USING THIS DYE

CROSS REFERENCE TO RELATED APPLICATIONS

This application is a national phase application based on PCT/EP2008/062711, filed Sep. 23, 2008, which claims the priority of French Patent Application No. 0757807, filed Sep. 24, 2007, and claims the benefit of U.S. Provisional Application No. 60/960,741, filed Oct. 11, 2007, the content of all of which is incorporated herein by reference.

The invention relates to the dyeing of keratin materials using dichromophore dyes with a carbonyl or heterocyclic linker.

It is known practice to dye keratin fibers, in particular human keratin fibers, by direct dyeing. The process conventionally used in direct dyeing comprises applying to the keratin fibers direct dyes which are colored or coloring molecules having an affinity for the fibers, allowing them to diffuse and then rinsing the fibers.

The direct dyes which are conventionally used are, for example, dyes of the nitrobenzene type, anthraquinone dyes, nitropyridine dyes, or dyes of the azo, xanthene, acridine, azine or triarylmethane type.

It is also known practice to use hemicyanin styryl direct dyes to strongly dye keratin fibers. These benzothiazolium or benzoimidazolium heteroaryl-group dyes are, for example, those described in patent applications EP 1166753 and EP 1166757.

The coloring of keratin fibers using these conventional direct dyes does not make it possible to significantly lighten keratin fibers.

The lightening of the color of dark keratin fibers to lighter shades, by optionally modifying the shade thereof, constitutes an important demand.

Conventionally, in order to obtain a lighter coloring, a chemical bleaching process is used. This process comprises treating the keratin fibers, such as the hair, with a strong oxidizing system, generally composed of hydrogen peroxide, possibly in combination with persalts, generally in an alkaline medium.

This bleaching system has the drawback of damaging the keratin fibers and of detrimentally affecting their cosmetic properties. The fibers in fact have a tendency to become rough, more difficult to disentangle and more brittle. Finally, the lightening or the bleaching of keratin fibers with oxidizing agents is incompatible with the treatments for modifying the shape of said fibers particularly in hair straightening treatments.

Another lightening technique comprises applying fluorescent direct dyes to dark hair. This technique, described in particular in documents WO 03/028685 and WO 2004/091473, makes it possible to retain the quality of the keratin fiber during the treatment. However, these fluorescent direct dyes do not exhibit satisfactory fastness with respect to outside agents.

In order to increase the fastness of direct colorings, it is known practice to use disulfide dyes, in particular imidazolium chromophore dyes in patent applications WO 2005/097051 or EP 1647580, and pyridinium/indolizinium styryl chromophore dyes in patent applications WO 2006/134043 and WO 2006/136617. These dyes use reducing agents to ensure good fastness. However, the reducing agents may present drawbacks in terms of odor, in terms of the user perceiving damage to the keratin fiber and in terms of multistep applications, including a fixing step with an oxidizing agent.

The aim of the present invention is to provide new systems for dyeing keratin materials, in particular human keratin fibers, especially dark hair, which do not have the drawbacks of the existing bleaching processes.

In particular, one aim of the invention is to provide direct dyeing systems for obtaining colorings, optionally with lightening effects or visible colorings, especially on dark keratin fibers, which are resistant to successive shampooing operations, which do not damage the keratin fibers and which do not detrimentally affect their cosmetic properties.

Another aim of the invention is to dye keratin materials chromatically, naturally and/or in a manner which is persistent with respect to outside attacks.

Another aim of the invention is to provide dyes which are stable in the formulation carriers, and which have better coloring from the root to the end on all types of hair, while at the same time being relatively nonselective.

This aim is achieved with the present invention, a subject of which is a process for dyeing keratin materials, in particular keratin fibers, especially human keratin fibers such as the hair, more particularly dark hair, comprising applying, to the keratin materials, a dye composition comprising, in a cosmetic medium, at least one dichromophore dye with a carbonyl or heterocyclic linker, chosen from the dyes of formula (I) below:

$$A\text{-}(L)_p\text{-}C_{sat}\text{—}S\text{—}Y\text{-}(L')_{p'}\text{-}Y\text{—}S\text{—}C_{sat}\text{-}(L)_p\text{-}A \qquad (I)$$

the organic or mineral acid salts, optical isomers and geometric isomers thereof, and the solvates such as hydrates:

in which formula (I):

A represents a radical containing at least one chromophore which is optionally cationic, colored, or colored and fluorescent;

L and L', which may be identical or different, represent:

a saturated or unsaturated, linear or branched $C_1$-$C_{20}$ hydrocarbon-based chain which is optionally substituted, optionally interrupted and/or optionally terminated at one or both of its ends with one or more divalent groups or combinations thereof chosen from —N(R)—, —O—, —S—, —C(O)— and —SO$_2$—, with R, R', which may be identical or different, being chosen from a hydrogen, and a $C_1$-$C_4$ alkyl, hydroxyalkyl and aminoalkyl radical; it being understood that said combination cannot form a disulfide bond —S—S—;

an arylene group, heteroarylene group, a cycloalkylene group, or a heterocycloalkylene group;

Y represents a carbonyl group —C(O)— or a heteroaryl group, which is cationic or noncationic, which comprises 5-13 members, which is optionally substituted, and which comprises from 1 to 5 heteroatoms chosen from oxygen, sulfur or nitrogen atoms; in particular, the divalent group —Y-(L')$_{p'}$-Y— is chosen from the divalent groups for which p' is 1, such as:

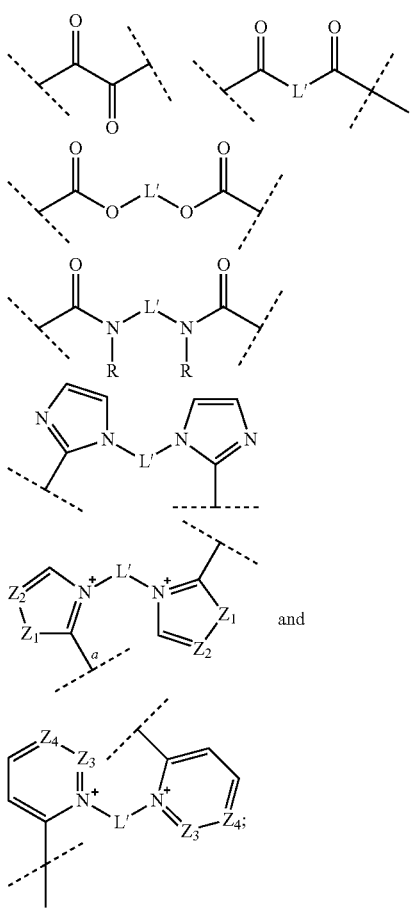

in which divalent groups:

Z₁ represents an oxygen or sulfur atom or a radical NR¹,
Z₂ represents a nitrogen atom or a radical CR²,
Z₃ represents a nitrogen atom or a radical CR³,
Z₄ represents a nitrogen atom or a radical CR⁴, with R², R³ and R⁴ representing a hydrogen or halogen atom, an optionally substituted (C₁-C₄)alkyl group or a (C₁-C₄)alkoxy, hydroxyl, (poly)hydroxy(C₂-C₄)alkoxy or C(O)—N(R') group, in which R and R' are as defined above, or an amino group, optionally substituted with one or two (hydroxy)(C₁-C₆) alkyl or hetero(C₅-C₇)cycloalkyl radicals, which may be identical or different, such as morpholino, etc., or else, two groups R¹ with R² and R³ with R⁴ form, together with the nitrogen and/or carbon atoms which bear them, a condensed aryl group such as benzo, R representing a hydrogen atom or an optionally substituted (C₁-C₄)alkyl group;

p and p', which may be identical or different, represent an integer equal to 0 or 1;

C_sat represents a linear or branched, optionally substituted C₁-C₁₈ alkylene chain.

Another subject of the invention is a dye composition for dyeing keratin fibers, comprising, in a cosmetic medium, at least one dye of formula (I) as defined above, and optionally a cosmetically acceptable acidic agent or basic agent; in particular, a basic agent.

A subject of the invention is also novel dyes of formula (I) as defined above.

Another subject of the invention is a multicompartment device in which a first compartment contains a dye composition containing at least one dye of formula (I) as defined above and a second compartment contains a cosmetically acceptable acidic or basic agent, in particular a basic agent.

The process of the invention makes it possible to obtain a coloring of the hair, without damage thereto, which is persistent with respect to shampooing operations, everyday attacks (sunlight, perspiration) and hair treatments. The dyeing process according to the invention also makes it possible to visibly color dark keratin materials, in particular dark human keratin fibers, especially dark hair. Furthermore, when the chromophore A is a chromophore derived from a fluorescent dye, it makes it possible to obtain lightening of keratin materials such as keratin fibers which is particularly visible on dark keratin fibers such as dark hair.

Moreover, the novel dyes according to the invention exhibit photostability and chemical stability which are very satisfactory. These dyes are soluble in the cosmetic media suitable for hair dyeing, and most particularly in water/ethanol mixtures. This process also makes it possible to dye bleached keratin fibers in a strong and chromatic manner.

The dyeing range obtained from the dyes of the invention also covers the basic shades that are the most popular in hair dyeing.

For the purpose of the present invention, the term "dark keratin material" is intended to mean that which exhibits a lightness L* measured in the C.I.E. L*a*b* system of less than or equal to 45, and preferably less than or equal to 40, given that, moreover, L*=0 is equivalent to black and L*=100 is equivalent to white.

For the purpose of the invention, the expression "naturally or artificially dark hair" is intended to mean whose tone height is less than or equal to 6 (dark blond) and preferably less than or equal to 4 (chestnut-brown).

The lightening of the hair is evaluated by the variation in "tone height" before and after application of the compound of formula (I). The notion of "tone" is based on the classification of the natural shades, one tone separating each shade from the shade immediately following or preceding it. This definition and the classification of the natural shades are well known to hair styling professionals and are published in the book "Science des traitements capillaires" [Hair Treatment Sciences], by Charles Zviak 1988, published by Masson, pp. 215 and 278.

The tone heights range from 1 (black) to 10 (very light blond), one unit corresponding to one tone; the higher the figure, the lighter the shade.

An artificially colored hair is a hair whose color has been modified by a dyeing treatment, for example dyeing with direct dyes or oxidation dyes.

For the purpose of the invention, the term "bleached hair" is intended to mean hair whose tone height is greater than 6 and preferably greater than 7.

For the purpose of the present invention, and unless otherwise indicated:

the "aryl" or "heteroaryl" radicals or the aryl or heteroaryl part of a radical may be substituted with at least one substituent chosen from:

a C₁-C₁₆, preferably C₁-C₈, alkyl radical optionally substituted with one or more radicals chosen from the radicals: hydroxyl, C₁-C₂ alkoxy, C₂-C₄(poly)hydroxyalkoxy, acylamino and amino substituted with two C₁-C₄ alkyl radicals, which may be identical or different, optionally bearing at least one hydroxyl group, or the two radicals possibly forming, with the nitrogen atom to which they are attached, a heterocycle comprising from 5 to 7 members, preferably 5 or 6 members, which is saturated or unsaturated, which is optionally substituted, and which optionally comprises another heteroatom which may be identical or different from the nitrogen;

a halogen atom such as chlorine, fluorine or bromine;

a hydroxyl group;

a $C_1$-$C_2$ alkoxy radical;

$C_1$-$C_2$ alkylthio radical;

a $C_2$-$C_4$ (poly)hydroxyalkoxy radical;

an amino radical;

a 5- or 6-membered heterocycloalkyl radical;

an optionally cationic 5- or 6-membered heteroaryl radical, preferably imidazolium, optionally substituted with a $C_1$-$C_4$ alkyl radical, preferably methyl;

an amino radical substituted with one or two $C_1$-$C_6$ alkyl radicals, which may be identical or different, optionally bearing at least:
  i) one hydroxyl group,
  ii) one amino group optionally substituted with one or two optionally substituted $C_1$-$C_3$ alkyl radicals, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen, —N(R)—C(O)R' in which the R radical is a hydrogen atom or a $C_1$-$C_4$ alkyl radical optionally bearing at least one hydroxyl group, and the R' radical is a $C_1$-$C_2$ alkyl radical;

(R)$_2$N—C(O)— in which the R radicals, which may or may not be identical, represent a hydrogen atom, or a $C_1$-$C_4$ alkyl radical optionally bearing at least one hydroxyl group;

R'SO$_2$—NR— in which the R radical represents a hydrogen atom or a $C_1$-$C_4$ alkyl radical optionally bearing at least one hydroxyl group, and the R' radical represents a $C_1$-$C_4$ alkyl radical or a phenyl radical;

(R)$_2$N—S(O)$_2$— in which the R radicals, which may or may not be identical, represent a hydrogen atom or a $C_1$-$C_4$ alkyl radical optionally bearing at least one hydroxyl group, a carboxylic radical in acid or salified form (preferably with an alkali metal or an ammonium, which is substituted or unsubstituted);

a cyano group;

a polyhaloalkyl group containing from 1 to 6 carbon atoms and from 1 to 6 halogen atoms, which may be identical or different; the polyhaloalkyl group is, for example, trifluoromethyl;

the cyclic or heterocyclic part of a nonaromatic radical may be substituted with at least one substituent, chosen from the groups:

hydroxyl;

$C_1$-$C_4$ alkoxy;

$C_1$-$C_4$ alkyl;

$C_2$-$C_4$ (poly)hydroxyalkoxy;

a $C_1$-$C_2$ alkylthio radical;

RC(O)—N(R')— in which the R' radical is a hydrogen atom or a $C_1$-$C_4$ alkyl radical optionally bearing at least one hydroxyl group, and the R radical is a $C_1$-$C_2$ alkyl radical or an amino radical substituted with two $C_1$-$C_4$ alkyl groups, which may be identical or different, optionally bearing at least one hydroxyl group;

RC(O)—O— in which the R radical is a $C_1$-$C_4$ alkyl radical or an amino radical substituted with one or two $C_1$-$C_4$ alkyl groups, which may be identical or different, optionally bearing at least one hydroxyl group, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen;

RO—C(O)— in which the R radical is a $C_1$-$C_4$ alkyl radical optionally bearing at least one hydroxyl group;

a cyclic or heterocyclic radical or a nonaromatic part of an aryl or heteroaryl radical may also be substituted with one or more oxo or thioxo groups;

an "aryl" radical represents a condensed or noncondensed, monocyclic or polycyclic group containing from 6 to 22 carbon atoms, and at least one ring of which is aromatic; preferably, the aryl radical is a phenyl, biphenyl, naphthyl, indenyl, anthracenyl or tetrahydronaphthyl;

a "heteroaryl radical" represents an optionally cationic, condensed or noncondensed, monocyclic or polycyclic group comprising from 5 to 22 members and from 1 to 6 heteroatoms chosen from a nitrogen, oxygen, sulfur and selenium atom, and at least one ring of which is aromatic; preferably, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphtho-imidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt;

a "cyclic or cycloalkyl radical" is a condensed or noncondensed, monocyclic or polycyclic, nonaromatic radical containing from 5 to 22 carbon atoms, possibly comprising one or more unsaturations; in particular, the cyclic radical is a cyclohexyl;

a "heterocyclic radical or heterocycle" is a condensed or noncondensed, monocyclic or poly-cyclic, nonaromatic radical containing from 5 to 22 members, comprising from 1 to 6 heteroatoms chosen from nitrogen, oxygen, sulfur and selenium;

the term "arylene", "heteroarylene", "cyclo-alkylene" and "heterocycloalkylene" is intended to mean divalent groups derived from the respective "aryl", "heteroaryl", "cycloalkyl" and "hetero-cycloalkyl" groups as defined above, it being possible for said divalent groups to be substituted with the same groups as those defined for the "aryl", "heteroaryl", "cycloalkyl" and "heterocycloalkyl" groups; in particular, the arylene group is a phenylene group, more particularly 1,4-phenylene or 1,3-phenylene; in particular, the arylene group is an indolylene group; the cycloalkylene group is a cyclohexylene group, and the heterocycloalkylene group is a piperazene group;

an "alkyl radical" is a linear or branched, $C_1$-$C_{16}$, preferably $C_1$-$C_8$, hydrocarbon-based radical;

an "alkylene chain" represents a divalent $C_1$-$C_{18}$ chain; in particular $C_1$-$C_6$, more particularly $C_1$-$C_2$ when the chain is linear; optionally substituted with one or more groups, which may be identical or different, chosen from hydroxyl, ($C_1$-$C_2$)alkoxy, (poly)hydroxy($C_2$-$C_4$)alkoxy (di)($C_1$-$C_2$) (alkyl)amino, $R^a$—$Z^a$—$C(Z^b)$— and $R^a$—$Z^a$—$S(O)_t$— groups, with $Z^a$, $Z^b$, which may be identical or different, representing an oxygen or sulfur atom or a group NR$^{a\prime}$, R$^a$ representing an alkali metal, a hydrogen atom or an alkyl group, or else it is absent if another part of the cationic molecule and R$^{a\prime}$ representing a hydrogen atom or an alkyl group, and t is 1 or 2;

a "saturated or unsaturated, optionally substituted C$_1$-C$_{20}$ hydrocarbon-based chain" represents a hydrocarbon-based, in particular C$_1$-C$_8$, chain optionally comprising one or more π double bonds, which may or may not be conjugated; in particular, the hydrocarbon-based chain is saturated; said chain is optionally substituted with one or more groups, which may be identical or different, chosen from hydroxyl, (C$_1$-C$_2$)alkoxy, (poly)hydroxy-(C$_2$-C$_4$)alkoxy(di)(C$_1$-C$_2$)(alkyl)amino, R$^a$—Z$^a$—C(Z$^b$)— and R$^a$—Z$^a$—S(O)$_t$— groups, with Z$^a$, Z$^b$, which may be identical or different, representing an oxygen or sulfur atom or a group NR$^{a\prime}$, R$^a$ representing an alkali metal, a hydrogen atom or an alkyl group, or else it is absent if another part of the cationic molecule and R$^{a\prime}$ representing a hydrogen atom or an alkyl group, and t is 1 or 2;

the expression "optionally substituted" assigned to the alkyl radical implies that said alkyl radical may be substituted with one or more radicals chosen from the radicals: i) hydroxyl; ii) C$_1$-C$_4$ alkoxy; iii) acylamino; iv) amino optionally substituted with one or two C$_1$-C$_4$ alkyl radicals, which may be identical or different, said alkyl radicals possibly forming, with the nitrogen atom which bears them, a heterocycle comprising from 5 to 7 members, optionally comprising another heteroatom which may or may not be different from nitrogen; v) or a quaternary ammonium group —N$^+$R'R"R'", M$^-$ for which R', R", R'", which may be identical or different, represent a hydrogen atom or a C$_1$-C$_4$ alkyl group, or else —N$^+$R'R"R'" forms a heteroaryl such as imidazolium optionally substituted with a C$_1$-C$_4$ alkyl group, and M$^-$ represents the anionic counterion;

an "alkoxy radical" is an alkyloxy or alkyl-O-radical for which the alkyl radical is a linear or branched, C$_1$-C$_{16}$, preferably C$_1$-C$_8$, hydrocarbon-based radical;

an "alkylthio radical" is an alkyl-S— radical for which the alkyl radical is a linear or branched, C$_1$-C$_{16}$, preferably C$_1$-C$_8$, hydrocarbon-based radical, when the alkylthio group is optionally substituted, this implies that the alkyl group is optionally substituted as defined above;

the limits delimiting the extent of the range of values are included in this range of values;

an "organic or mineral acid salt" is more particularly chosen from a salt derived from cosmetically acceptable acids such as: i) from hydrochloric acid HCl; ii) from hydrobromic acid HBr; iii) from sulfuric acid H$_2$SO$_4$; iv) from alkylsulfonic acids: Alk-S(O)$_2$OH such as methylsulfonic acid and ethylsulfonic acid; v) from arylsulfonic acids: Ar—S(O)$_2$OH such as from benzenesulfonic acid and from toluenesulfonic acid; vi) from citric acid; vii) from succinic acid; viii) from tartaric acid; ix) from lactic acid; x) from alkoxysulfinic acids: Alk-O—S(O)OH such as from methoxysulfinic acid and from ethoxysulfinic acid; xi) from aryloxysulfinic acids such as from tolueneoxysulfinic acid and from phenoxysulfinic acid; xii) from phosphoric acid H$_3$PO$_4$; xiii) from acetic acid CH$_3$C(O)OH; xiv) from triflic acid CF$_3$SO$_3$H and xv) from tetrafluoroboric acid HBF$_4$;

an "anionic counterion" is an anion or an anionic group associated with the cationic charge of the dye; more particularly, the anionic counterion is chosen from: i) halides such as chloride or bromide; ii) nitrates; iii) sulfonates, among which are C$_1$-C$_6$ alkyl sulfonates: Alk-S(O)$_2$O— such as methyl sulfonate or mesylate and ethyl sulfonate; iv) aryl sulfonates: Ar—S(O)$_2$O$^-$ such as benzene sulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) arylsulfates: Ar—O—S(O)O$^-$ such as benzenesulfate and toluenesulfate; xi) alkoxysulfates: Alk-O—S(O)$_2$O$^-$ such as methoxy sulfate and ethoxy sulfate; xii) aryloxysulfates: Ar—O—S(O)$_2$O$^-$; xiii) phosphate; xiv) acetate; xv) triflate; and xvi) borates such as tetrafluoroborate;

the "solvates" represent the hydrates and also the association with linear or branched C$_1$-C$_4$ alcohols such as ethanol, isopropanol or n-propanol.

The dyes of formula (I) as defined above are dyes, i.e. compounds comprising chromophores A capable of absorbing light in the visible spectrum. Furthermore, some dyes of the invention of formula (I) are, in addition, fluorescent dyes, i.e. they comprise chromophores A capable of absorbing light in the UV radiation or visible range at a wavelength $\lambda_{abs}$ of between 250 and 800 nm and capable of re-emitting light in the visible range at an emission wavelength greater than that absorbed $\lambda_{em}$ of between 400 and 800 nm. The difference between the absorption wavelength and the emission wavelength is commonly referred to as Stoke's shift, which is between 1 nm and 100 nm.

Preferably, the dyes which are also fluorescent of formula (I) of the invention are dyes capable of absorbing in the visible range $\lambda_{abs}$ of between 400 and 800 nm and of re-emitting in the visible range $\lambda_{em}$ of between 400 and 800 nm. More preferably, the dyes of formula (I) are dyes capable of absorbing at a $\lambda_{abs}$ of between 420 and 550 nm and of re-emitting in the visible range at a $\lambda_{em}$ of between 470 and 600 nm.

By way of chromophores A which can be used in the present invention, mention may be made of the radicals derived from acridine, acridone, anthranthrone, anthra-pyrimidine, anthraquinone, azine, azo, azomethine, benzanthrone, benzimidazole, benzimidazolone, benz-indole, benzoxazole, benzopyran, benzothiazole, benzoquinone, bisazine, bisisoindoline, carboxanilide, coumarin, cyanin (such as azacarbocyanin, diazacarbo-cyanin, diazahemicyanin/hydrazone, hemicyanin/styryl, tetraazacarbocyanin), diazine, diketopyrrolopyrrole, dioxazine, diphenylamine, diphenylmethane, dithiazine, flavonoid, such as flavanthrone and flavone, fluorindine, formazan, hydrazone, in particular arylhydrazone, hydroxy ketone, indamine, indanthrone, indigoid and pseudoindigoid, indophenol, indoaniline, isoindoline, isoindolinone, isoviolanthrone, lactone, methine, naphthalimide, naphthanilide, naphtholactam, naphthoquinone, nitro, in particular nitro(hetero)-aromatic, oxadiazole, oxazine, perilone, perinone, perylene, phenazine, phenothiazine, phthalocyanin, polyene/carotenoid, porphyrin, pyranthrone, pyrazol-anthrone, pyrazolone, pyrimidinoanthrone, pyronine, quinacridone, quinoline, quinophthalone, squarane, stilbene, thiazine, thioindigo, thiopyronine, triarylmethane and xanthene dyes.

By way of fluorescent chromophores A that can be used in the present invention, mention may be made of the radicals derived from benzimidazolone, benzoxazole, coumarin, difluoro-{2-[(2H-pyrrol-2-ylidene-kN)methyl]-1H-pyrrolato-kN}boron (BODIPY®), diketopyrrolopyrrols, fluorindine, (poly)methine (in particular cyanin and styryl/hemicyanin), naphthalimide, naphthanilide, naphthylamine (such as dansyl), oxadiazole, oxazine, perilone, perinone, stilbene and xanthene dyes.

Mention may also be made of the fluorescent dyes described in documents EP 1133975, WO 03/029359, EP 860636, WO 95/01772, WO 95/15144, EP 714954 and those listed in the encyclopedia "*The chemistry of synthetic dye*" by K. Venkataraman, 1952, Academic Press vol. 1 to 7, in the encyclopedia "*Kirk Othmer*" "Chemical technology", chapter "Dyes and Dye Intermediate", 1993, Wiley and Sons, and in various chapters of the encyclopedia "*Ullmann's Encyclopedia of Industrial Chemistry*" 7th edition, Wiley and Sons, in *The Handbook—A Guide to Fluorescent Probes and Labeling Technologies*, 10th ed. Molecular Probes/Invitrogen—Oregon 2005 available on the Internet or in the previous printed editions.

Among the nitro chromophores A that can be used according to the invention, mention may be made, in a nonlimiting manner, of the radicals derived from the following dyes:
1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethyl-amino)benzene
1-β-hydroxyethylamino-2-nitro-4-aminobenzene
1-β-hydroxyethylamino-2-nitro-4-(ethyl) (β-hydroxy-ethyl)aminobenzene
1-amino-3-methyl-4-β-hydroxyethylamino-6-nitrobenzene
1-amino-2-nitro-4-β-hydroxyethylamino-5-chloro-benzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo chromophores that can be used according to the invention, mention may be made of the radicals derived from the cationic azo dyes described in patent applications WO 95/15144, WO 95/01772 and EP 714954.

Among the azo chromophores, mention may also be made of those described in the Colour Index International 3rd edition, and in particular the following compounds:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone chromophores A, those mentioned in the abovementioned Colour Index International are suitable, and among the latter, mention may be made, inter alia, of the radicals derived from the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine chromophores A, those listed in the International Colour Index are suitable, and for example the radicals derived from the following dyes:
Basic Blue 17
Basic Red 2.

Among the triarylmethane chromophores A that can be used according to the invention, mention may be made, in addition to those listed in the Colour Index, of the radicals derived from the following dyes:
Basic Green 1
Acid Blue 9
Basic Violet 3
Basic Violet 14
Basic Blue 7
Acid Violet 49
Basic Blue 26
Acid Blue 7.

Among the indoamine chromophores A that can be used according to the invention, mention may be made of the radicals derived from the following dyes:
2-β-hydroxyethylamino-5-[bis(β-4'-hydroxyethyl)-amino]anilino-1,4-benzoquinone
2-β-hydroxyethylamino-5-(2'-methoxy-4'-amino)-anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethylcarbamylmethyl)amino]phenylureido-6-methyl-1,4-benzoquinone imine.

Mention may also be made of the chromophores described in documents U.S. Pat. No. 5,888,252, EP 1133975, WO 03/029359, EP 860636, WO 95/01772, WO 95/15144 and EP 714954. Mention may also be made of those listed in the encyclopedia "The chemistry of synthetic dye" by K. Venkataraman, 1952, Academic Press vol. 1 to 7, in the encyclopedia "Kirk Othmer" "Chemical technology", chapter "Dyes and Dye Intermediate", 1993, Wiley and Sons, and in various chapters of the encyclopedia "Ullmann's Encyclopedia of Industrial Chemistry" 7th edition, Wiley and Sons.

Preferably, the chromophores A are chosen from those derived from dyes of azo, anthraquinone and hydrazone type.

Preferably, the fluorescent chromophores A are chosen from those derived from dyes of coumarin, (poly)methine (in particular cyanin and styryl/hemicyanin) and naphthalimide type.

According to one variant, A of formula (I) contain at least one cationic radical borne by or included in at least one of the chromophores.

Preferably, the cationic radical is a quaternary ammonium.

These cationic radicals are, for example, an alkyl-ammonium, acridinium, benzimidazolium, benzobistriazolium, benzopyrazolium, benzopyridazinium, benzoquinolium, benzothiazolium, benzotriazolium, benzoxazolium, bipyridinium, bistetrazolium, dihydrothiazolium, imidazopyridinium, imidazolium, indolium, isoquinolium, naphthoimidazolium, naphthooxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium radical.

Examples of cationic chromophores A that can be used in the present invention have been mentioned above. Other examples are given in patent applications WO 95/01772, WO 95/15144, EP 714954, EP 318294 and WO 03/029359.

According to a specific embodiment, the radicals A, A' in formula (I) or (II) comprise at least one cationic azo chromophore, described, for example, in EP 850636, FR 2788433, EP 920856, WO 9948465, FR 2757385, EP 850637, EP 918053, WO 9744004, FR 2570946, FR 2285851, DE 2538363, FR 2189006, FR 1560664, FR 1540423, FR 1567219, FR 1516943, FR 1221122, DE 4220388, DE 4137005, WO 0166646, U.S. Pat. No. 5,708, 151, WO 9501772, WO 515144, GB 1195386, U.S. Pat. No. 3,524,842, U.S. Pat. No. 5,879,413, EP 1062940, EP 1133976, GB 738585, DE 2527638, FR 2275462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

Preferably, the chromophores are chosen from those derived from dyes of azo, azomethine and cyanin type (such as azacarbocyanin, diazacarbocyanin, diaza-hemicyanin/hydrazone, hemicyanin/styryl dyes).

According to one variant of the invention, the dyes of formula (I) are cationic dyes comprising at least one quaternary ammonium radical A which represents:

with:

W representing a heteroaryl, comprising a quaternary ammonium, optionally substituted preferably with one or more $(C_1\text{-}C_4)$alkyl groups;

Ar represents i) a 5- or 6-membered (hetero)aryl radical of phenyl or pyridium type, or ii) a (hetero)aromatic bicycle of naphthyl, benzopyridinyl, indolinyl or benzoindolinyl type, optionally substituted with one or more halogen atoms, preferably chlorine or fluorine; with one or more preferably $C_1\text{-}C_4$ alkyl groups; with one or more hydroxyl groups; with one or more alkoxy groups, with one or more hydroxyalkyl groups, with one or more amino or (di)alkylamino groups, preferably with the alkyl part being $C_1\text{-}C_4$;

Z representing an oxygen or sulfur atom, or a group NR' with R' representing a (hydroxy)$(C_1\text{-}C_4)$alkyl group.

According to another specific embodiment of the invention, the cationic fluorescent dyes of the invention of formula (I) comprise at least one fluorescent chromophore and a quaternary ammonium radical:

A represents:

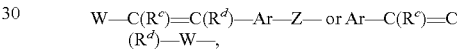

with:

W representing a heterocycle or a heteroaryl, comprising a quaternary ammonium;

Ar represents i) a 5- or 6-membered (hetero)aryl radical of phenyl or pyridinium type, or ii) a (hetero)aromatic bicycle of naphthyl, benzopyrydinium, indolinyl or benzoindolinyl type, optionally substituted with one or more halogen atoms, preferably chlorine or fluorine; with one or more preferably $C_1\text{-}C_4$ alkyl groups; with one or more hydroxyl groups; with one or more alkoxy groups, with one or more hydroxyalkyl groups, with one or more amino or (di)alkylamino groups, preferably with the alkyl part being $C_1\text{-}C_4$, with one or more acylamino groups; with one or more heterocycloalkyl or heteroaryl groups comprising 5 or 6 members, preferably chosen from pyrrolidinyl, piperazinyl, piperidinyl and imidazolinyl;

$R^c, R^d$, which may be identical or different, represent a hydrogen atom or a $C_1\text{-}C_4$ alkyl group;

Z representing an oxygen or sulfur atom, or a group NR' with R' representing a (hydroxy)$(C_1\text{-}C_4)$alkyl group.

According to a specific embodiment, Z is in the para-position on Ar relative to the azo function or of the double bond —$C(R^c)$=$C(R^d)$—.

Another specific embodiment of the invention relates to the dyes of formula (I) for which p is 0. Another embodiment relates to the dyes of formula (I) for which p is 1.

According to a specific embodiment of the invention, the dyes of formula (I) are such that Y represents a carbonyl group, L' represents a $C_2\text{-}C_6$ alkylene, such as ethylene, or arylene, such as phenylene, group optionally interrupted with 1 or 2 heteroatoms such as oxygen and optionally terminated at each of its ends with a heteroatom, such as oxygen, or NR with R representing a hydrogen atom or a $(C_1\text{-}C_4)$alkyl group.

By way of example, mention may be made of the dyes of formula (I):

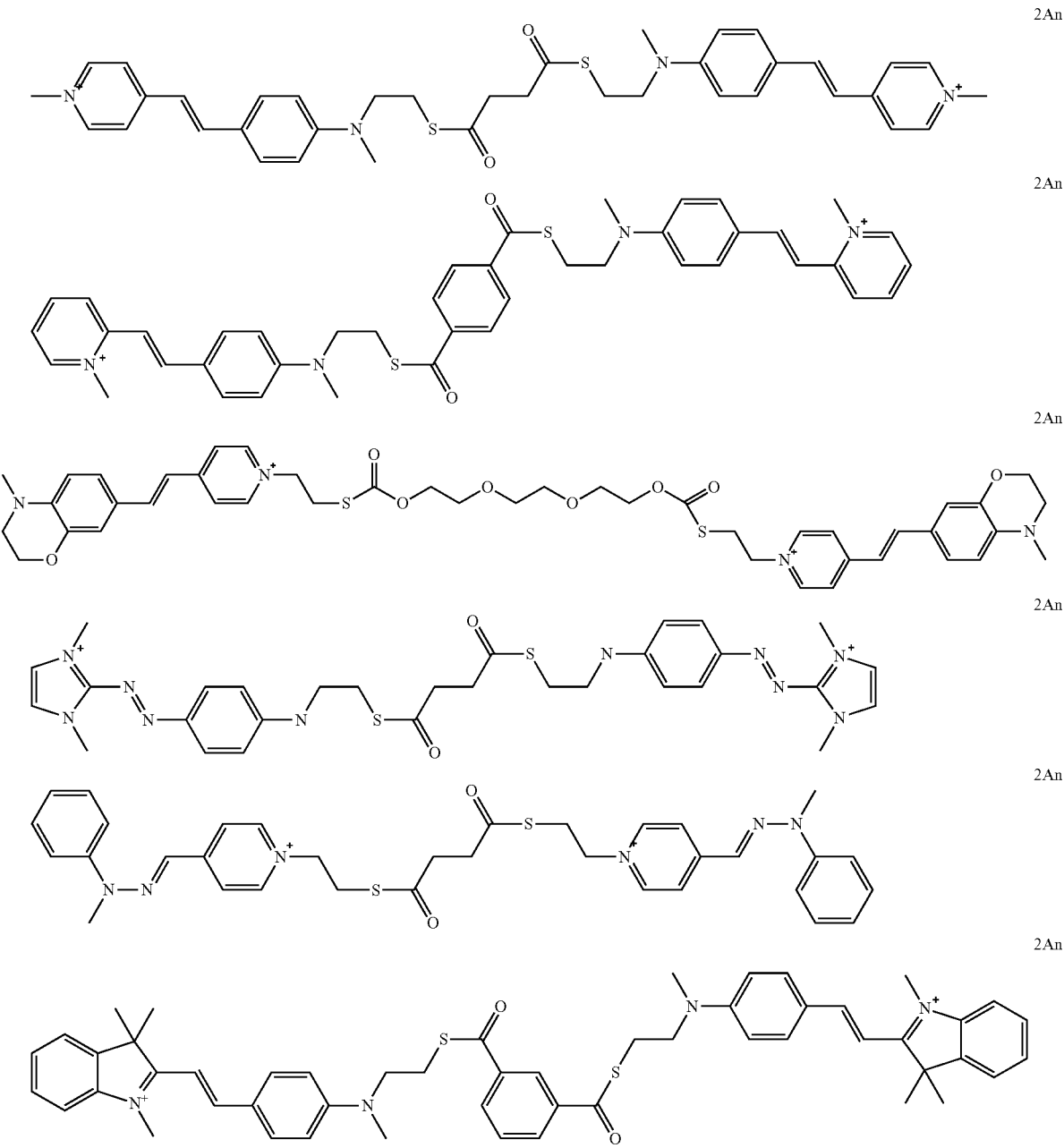

with An representing an anionic counterion.

For all the exemplary embodiments, which follow, for preparation of the novel dyes of formula (I), those skilled in the art know how to pre-protect the reactive functions such as ketone functions and then to deprotect them for the needs of the synthesis reaction, by the known conventional methods of protection/deprotection such as those described in the books mentioned above by T. W. Greene John Willey & Sons ed., NY, 1981, or P. Kocienski "*Protecting Groups*", P. Kocienski, Thieme, 3rd ed., 2005.

These dyes can be prepared according to methods known to those skilled in the art, such as, for example, "Colour Chemistry, Heinrich Zollinger, Wiley-VCH, Weinheim, 2003".

According to a first possibility, a compound C1 comprising at least two nucleophilic functions Nu can be reacted with a sufficient amount of a "reactive chromophore A" or of a compound comprising such a "reactive chromophore", in other words comprising an electrophilic function E, so as to form a covalent bond or a divalent linking group Σ:

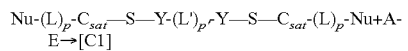

$$\text{Nu-(L)}_{p'}\text{-C}_{sat'}\text{—S—Y-(L')}_{p'}\text{-Y—S—C}_{sat'}\text{-(L)}_{p}\text{-Nu+A-}$$
$$\text{E} \rightarrow [\text{C1}]$$

$$\text{A-}\Sigma\text{-(L)}_{p'}\text{-C}_{sat'}\text{—S—Y-(L')}_{p'}\text{-Y—S—C}_{sat'}\text{-(L)}_{p}\text{-}\Sigma\text{-A}$$

with Nu representing a nucleophilic group; E representing an electrophilic group; A, Y, L, L', $C_{sat}$, p and p' as defined above, and, by way of example, the covalent bonds or divalent groups Σ that can be generated are listed in the table below based on condensation of electrophiles with nucleophiles:

| Electrophiles E | Nucleophiles Nu | Σ Covalent bonds |
|---|---|---|
| Activated esters* | Amines | Carboxamides |
| Acyl nitrides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Alkylamines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-Part with Part representing a leaving group such as oxysuccinimidyl, oxybenzotriazolyl, aryloxy which is optionally substituted;
**the acyl nitrides may rearrange to give isocyanates.

Reference may be made especially to the book *Advanced Organic Chemistry*, J. March, 4th Ed., John Willey & Sons, 1992.

In accordance with other variants, it is possible to synthesize the dyes of the invention according to the following reaction schemes:

$$\text{Nu-}(L)_p\text{-}C_{sat}\text{—S—Y-}(L')_{p'}\text{-Y—S—}C_{sat}\text{-}(L_p)\text{-Nu+2A-}$$
$$\text{E} \rightarrow \text{A-}\Sigma\text{-}(L)_p\text{-}C_{sat}\text{—S—Y-}(L')_{p'}\text{-Y—S—}C_{sat}\text{-}(L)_p\text{-}\Sigma\text{-A}$$

with A, Y, L, L', p, p', $C_{sat}$, Σ, Nu and E as defined above;

$$2\text{A-}\Sigma\text{-}(L)_p\text{-}C_{sat}\text{—SH+Lg-Y-}(L')_{p'}\text{-Y-Lg} \rightarrow \text{A-}\Sigma\text{-}(L)_p\text{-}C_{sat}\text{—S—Y-}(L')_{p'}\text{-Y—S—}C_{sat}\text{-}(L)_p\text{-}\Sigma\text{-A}$$

with A, Y, L, L', p, p', $C_{sat}$ and Σ as defined above; Lg represents a nucleofuge leaving group such as halide, in particular bromide or chloride, mesylate or tosylate;

$$\text{E-}(L)_p\text{-}C_{sat}\text{—S—Y-}(L')_{p'}\text{-Y—S—}C_{sat}\text{-}(L)_p\text{-E+2A-}\text{Nu} \rightarrow \text{A-}\Sigma\text{-}(L)_p\text{-}C_{sat}\text{—S—Y-}(L')_{p'}\text{-Y—S—}C_{sat}\text{-}(L)_p\text{-}\Sigma\text{-A}$$

with A, Y, L, L', p, p', $C_{sat}$, Σ, Nu and E as defined above;

$$\text{E-}(L)_p\text{-}C_{sat}\text{—S—Y'+A-Nu} \rightarrow \text{A-}\Sigma\text{-}(L)_p\text{-}C_{sat}\text{—S—Y'} \rightarrow \text{A-}\Sigma\text{-}(L)_p\text{-}C_{sat}\text{—SH}$$

with Y' representing a thiol-function-protecting group, and A, L, p, $C_{sat}$, Σ, Nu and E as defined above;

$$2\text{A-}\Sigma\text{-}(L)_p\text{-}C_{sat}\text{—SH+Lg-Y-}(L')_{p'}\text{-Y-Lg} \rightarrow \text{A-}\Sigma\text{-}(L)_p\text{-}C_{sat}\text{—S—Y-}(L')_{p'}\text{-Y—S—}C_{sat}\text{-}(L)_p\text{-}\Sigma\text{-A}$$

with A, Y, L, L', p, p', $C_{sat}$, Lg and Σ as defined above.

Another subject of the invention relates to a composition comprising at least one dye of formula (I). In addition to the presence of at least one dye of formula (I), the composition of the invention may also contain a cosmetically acceptable acidic or basic agent; in particular a basic agent.

The pH of the dye composition is generally between 5 and 12 approximately, preferably between 9 and 11. It can be adjusted to the desired value by means of acidifying or basifying agents as defined below, normally used in the dyeing of keratin fibers, or alternatively using conventional buffer systems.

Among the cosmetically acceptable acidic or acidifying agents, mention may be made of mineral or organic acids such as hydrochloric acid HCl, hydrobromic acid HBr, sulfuric acid $H_2SO_4$, phosphoric acid $H_3PO_4$, alkylsulfonic acids: Alk-$S(O)_2$OH such as methylsulfonic acid and ethylsulfonic acid, arylsulfonic acids: Ar—$S(O)_2$OH such as benzenesulfonic acid and toluenesulfonic acid, citric acid, succinic acid; tartaric acid; lactic acid; alkoxysulfinic acids: Alk-O—S(O)OH such as methoxysulfinic acid and ethoxysulfinic acid; aryloxysulfinic acids such as tolueneoxysulfinic acid and phenoxysulfinic acid; carboxylic acids such as acetic acid $CH_3C(O)OH$, tartaric acid, citric acid, lactic acid, triflic acid; $CF_3SO_3H$ and tetrafluoroboric acid $HBF_4$.

Among the cosmetically acceptable basic or basifying agents, mention may be made, by way of example, of aqueous ammonia, alkali metal carbonates, alkanolamines such as mono-, di- and triethanolamines and also derivatives thereof, sodium hydroxide or potassium hydroxide, and the compounds of formula (γ) below:

in which $W_a$ is a propylene residue optionally substituted with a hydroxyl group or a $C_1$-$C_4$ alkyl radical; $R_{a1}$, $R_{a2}$, $R_{a3}$ and $R_{a4}$, which may be identical or different, represent a hydrogen atom, or a $C_1$-$C_4$ alkyl or $C_1$-$C_4$ hydroxyalkyl radical.

The dye composition that can be used in the invention generally contains an amount of dye of formula (I) of between 0.001% and 50% relative to the total weight of the composition. Preferably, this amount is between 0.005% and 20% by weight, and even more preferably between 0.01% and 5% by weight, relative to the total weight of the composition.

The dye composition may also contain additional direct dyes. These direct dyes are, for example, chosen from neutral, acidic or cationic nitrobenzene direct dyes, neutral, acidic or cationic azo direct dyes, tetraazapentamethine dyes, neutral, acidic or cationic quinone, in particular anthraquinone dyes, azine direct dyes, triarylmethane direct dyes, indoamine direct dyes and natural direct dyes.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenindin. Extracts or decoctions containing these natural dyes, and in particular poultices or henna-based extracts, may also be used.

The dye composition may contain one or more oxidation bases and/or one or more couplers conventionally used for dyeing keratin fibers.

Among the oxidation bases, mention may be made of para-phenylenediamines, bisphenylalkylenediamines, para-aminophenols, bis-para-aminophenols, orthoaminophenols, heterocyclic bases, and addition salts thereof.

Among these couplers, mention may in particular be made of meta-phenylenediamines, meta-aminophenols, meta-diphenols, naphthalene couplers, heterocyclic couplers, and addition salts thereof.

The coupler(s) is (are) each generally present in an amount of between 0.001% and 10% by weight of the total weight of the dye composition, preferably between 0.005% and 6%.

The oxidation base(s) present in the dye composition is (are) in general each present in an amount of between 0.001% and 10% by weight of the total weight of the dye composition, preferably between 0.005% and 6% by weight.

In general, the addition salts of the oxidation bases and of the couplers that can be used in the context of the invention are in particular chosen from addition salts with an acid, such as hydrochlorides, hydro-bromides, sulfates, citrates, succinates, tartrates, lactates, tosylates, benzenesulfonates, phosphates and acetates, and addition salts with a base, such as hydroxides of an alkali metal such as sodium or potassium, aqueous ammonia, amines or alkanolamines.

The medium suitable for dyeing, also called dye support, is a cosmetic medium generally containing water or a mixture of water and at least one organic solvent. By way of organic solvent, mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

The solvents, when they are present, are preferably present in proportions of preferably between 1% and 99% by weight approximately, relative to the total weight of the dye composition, and even more preferably between 5% and 95% by weight approximately.

The dye composition may also contain various adjuvants conventionally used in hair-dyeing compositions, such as anionic, cationic, nonionic, amphoteric or zwitterionic surfactants or mixtures thereof, anionic, cationic, nonionic, amphoteric or zwitterionic polymers, or blends thereof, mineral or organic thickeners, and in particular anionic, cationic, nonionic and amphoteric associative polymer thickeners, antioxidants, penetrating agents, sequestering agents, fragrances, buffers, dispersing agents, conditioning agents such as, for example, modified or unmodified, volatile or nonvolatile silicones, such as amino silicones, film-forming agents, ceramides, preservatives, opacifiers or conductive polymers.

The above adjuvants are in general present in an amount, for each of them, of between 0.01% and 20% by weight relative to the weight of the composition.

Of course, those skilled in the art will take care to select this or these possible additional compounds in such a way that the advantageous properties intrinsically associated with the dye composition in accordance with the invention are not, or are not substantially, impaired by the addition(s) envisaged.

The dye composition may be in various forms, such as in the form of a liquid, a cream or a gel, or in any other form suitable for dyeing keratin fibers, and in particular the hair.

Another subject of the invention is a dyeing process consisting in applying a cosmetic composition comprising at least one dye of formula (I) as defined above to the keratin fibers, optionally in the presence of an acidic or basic agent, preferably a basic agent.

The process for dyeing keratin fibers, in particular dark keratin fibers, according to the invention consists in applying, to the keratin materials, a dye composition comprising, in a suitable cosmetic medium, at least one dye of formula (I) or at least one fluorescent dye of formula (I).

According to a specific embodiment, in the process of the invention, the basic agent is applied as a post-treatment after the application of the composition containing at least one dye of formula (I).

This post-treatment may be of short duration, in particular from 1 second to 30 minutes, preferably from 1 minute to 15 minutes, with an acidic or basic agent.

According to a specific embodiment, in the process of the invention, the basic agent is applied at the same time as the application of the composition containing at least one dye of formula (I).

According to another specific embodiment, in the process of the invention, a reducing agent is applied as post-treatment after the application of the composition containing at least one dye of formula (I).

According to another specific embodiment, in the process of the invention, a reducing agent is applied as a pretreatment before the application of the composition containing at least one dye of formula (I).

According to another specific embodiment, in the process of the invention, a reducing agent is applied at the same time as the composition containing at least one dye of formula (I).

This reducing agent may be chosen from thiols, for example cysteine, homocysteine or thiolactic acid, the salts of these thiols, phosphines, bisulfite, sulfites, thioglycolic acid, and also its esters, in particular glyceryl monothioglycolate, and thioglycerol. This reducing agent may also be chosen from borohydrides and derivatives thereof, for instance the salts of borohydride, of cyanoborohydride, of triacetoxyborohydride or of trimethoxyborohydride: sodium salts, lithium salts, potassium salts, calcium salts, quaternary ammonium (tetramethylammonium, tetraethylammonium, tetra-n-butylammonium or benzyltriethylammonium) salts; and catechol borane.

A specific embodiment of the invention relates to a process in which the fluorescent dye of formula (I) is applied directly to the hair without reducing agents, free of acidic or basic post-treatment.

A treatment with an oxidizing agent may optionally be combined. Preferably the process of dyeing keratin fibers according to the invention comprises an additional step consisting in applying an oxidizing agent to the keratin fibers. Any type of oxidizing agent conventional in the field may be used. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases and 4-electron oxygenases such as laccases. The use of hydrogen peroxide is particularly preferred. The duration of such treatment is between 1 second and 40 minutes, preferably between 15 seconds and 15 minutes.

The application of the dye composition according to the invention is generally carried out at ambient temperature. It may, however, be carried out at temperatures ranging from 20 to 180° C.

A subject of the invention is also a multicompartment dyeing device or dyeing "kit" in which a first compartment contains a dye composition comprising at least one of formula (I) and a second compartment contains a cosmetically acceptable acidic or basic agent capable of freeing the thiol function of the heterocyclic or carbonyl linker.

One of these compartments may also contain one or more other dyes of direct dye or oxidation dye type.

The invention also relates to a multicompartment device in which a first compartment contains a dye composition comprising at least one dye of formula (I); a cosmetically acceptable acidic or basic agent capable of freeing the thiol function of the carbonyl or heterocyclic linker; and a third compartment contains an oxidizing agent.

Each of the devices mentioned above may be equipped with a means for delivering the desired mixture to the hair, for example such as the devices described in patent FR 2 586 913.

The examples which follow serve to illustrate the invention without, however, being limiting in nature but in the limit of the scope of the object claimed. The dyes of the examples hereinafter have been entirely characterized by conventional spectroscopic and spectrometric methods.

EXAMPLES

Synthesis Examples

Example 1

Synthesis of 1,1'-[(1,4-Dioxobutane-1,4-diyl)bis(sulfanediylethane-2,1-diyl)]bis(4-{[methyl(phenyl)hydrazono]methyl}pyridinium) dichloride [1]

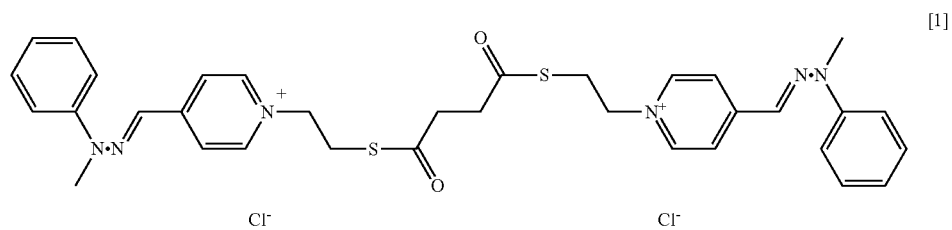

Synthesis Scheme

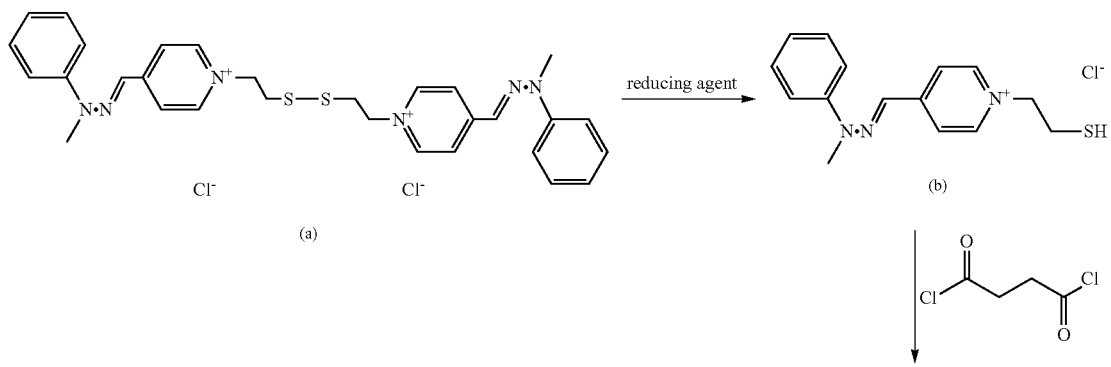

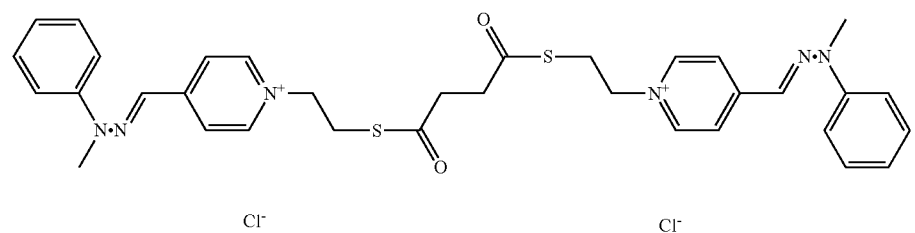

Procedure

Stage 1: Synthesis of 4-{[methyl(phenyl)hydrazono]-methyl}-1-(2-sulfanylethyl)pyridinium chloride 1 g of compound [a] is dissolved in 50 ml of a 1/1 mixture of water/ethanol. 2 eq. of 3-[bis(2-carboxy-ethyl)phosphino]propanoic acid hydrochloride hydrate in solution in 20 ml of water and 4 eq. of sodium bicarbonate in solution in 10 ml of water are added to the mixture. After stirring for 30 minutes at 40° C. under an inert atmosphere, the reaction mixture is poured into 2-propanol and the yellow precipitate is filtered off.

Stage 2: Synthesis of 1,1'-[(1,4-dioxobutane-1,4-diyl)bis(sulfanediylethane-2,1-diyl)]bis(4-{[methyl(phenyl)hydrazono]methyl}pyridinium) dichloride [1]

200 mg of compound [b] and 2 eq. of trimethylamine are diluted in 10 ml of N-methylpyrrolidinone (NMP). At 0° C., 0.5 eq. of succinyl chloride (CAS 543-20-4) diluted in 5 ml of NMP (anhydrous) is added dropwise to the reaction medium with vigorous stirring. The stirring is continued at ambient temperature for 6 h and the reaction mixture is then poured into 2-propanol and the yellow precipitate is filtered off.

Example 2

Synthesis of 4,4'-{1,4-phenylenebis[carbon-ylsulfanediylethane-2,1-diyl(methylimino)-4,1-phenyleneethene-2,1-diyl]}bis(1-methyl-pyridinium) bis(methyl) sulfate [2]

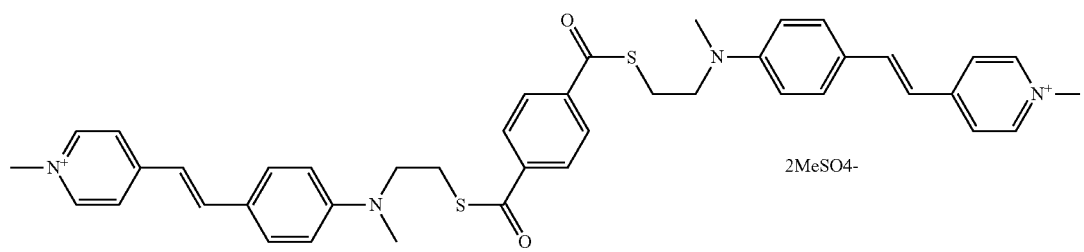

Synthesis scheme

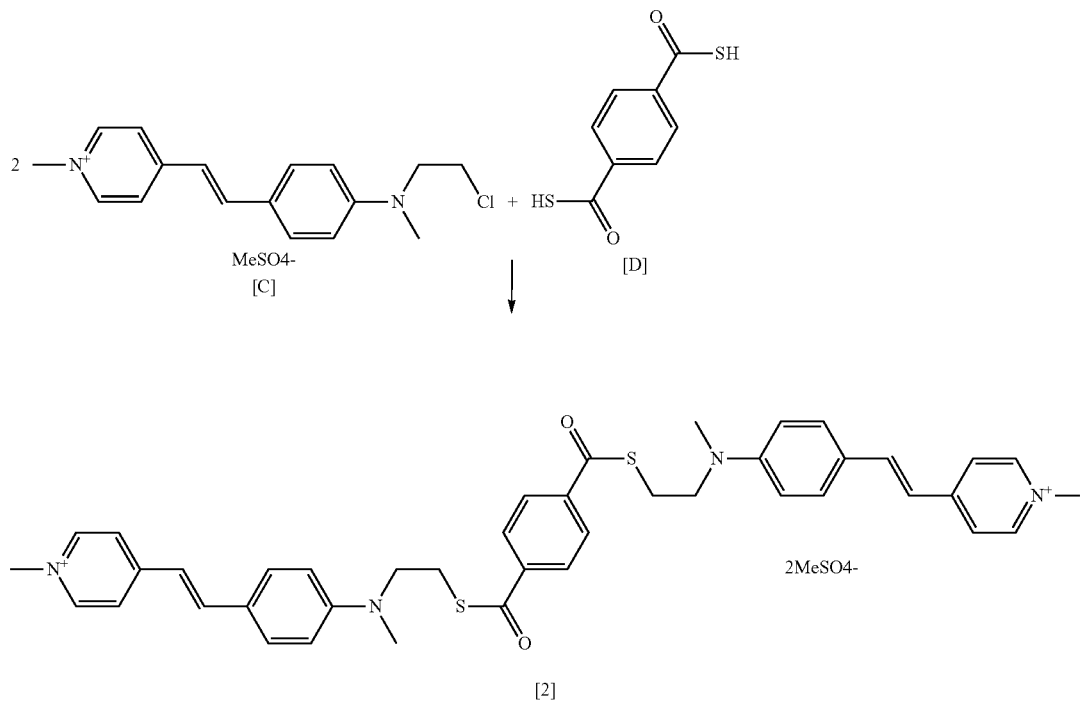

Procedure 500 mg of compound [C] and 2 eq. of trimethylamine are diluted in 25 ml of N-methylpyrrolidinone (NMP). At 0° C., 0.5 eq. of dithioterephthalic acid [D] (CAS 1076-98-8) diluted in 5 ml of NMP (anhydrous) is added dropwise to the reaction medium with vigorous stirring. The stirring is continued at ambient temperature for 4 h and the reaction mixture is then poured into 2-propanol and the bright orange precipitate is filtered off. The analyses indicate the expected product [2].

Dyeing Examples

The dye compositions were prepared in the following proportions

| Solution 1 | |
|---|---|
| Hydroxyethylcellulose Natrosol 250MR | 0.72 g |
| C8/C10 (50:50) alkyl hydroxyethylcellulose CG110 | 5 g |
| Benzyl alcohol | 4 g |
| Polyethylene glycol 400 | 4 g |
| Water | qs 100 g |

| Solution 2: pH 7 BUFFER | |
|---|---|
| KH$_2$PO$_4$ | 0.026 mol/l |
| Na$_2$PO$_4$ | 0.041 mol/l |
| Demineralized water | qs 500 ml |

The dye compositions are obtained by dissolving dye [1] or [2] indicated above (5×10$^{-3}$ mol/l) in solution 1 and then adding an equivalent volume of buffer solution 2.

Each composition is applied to bleached hair (SA40), natural gray hair comprising 90% white hairs, permanent-waved gray hair comprising 90% white hairs (1 g of lock per 6 g of solution) and dark hair (TH4). After a leave-in time of 30 min, the locks are rinsed. Next, solution 3 is applied to bleached hair (SA40), natural gray hair comprising 90% white hairs, permanent-waved gray hair comprising 90% white hairs and dark hair (TH4) (1 g of lock per 6 g of solution) and the hair is heated to 45° C. After a leave-in time of 60 min, the locks are rinsed, washed with a standard shampoo, rinsed again, and then dried.

| Solution 3: | |
|---|---|
| Ammonium chloride (NH$_4$Cl) | 5.4 g |
| Aqueous ammonia as a solution at 20% | qs pH = 9.5 |
| Demineralized water | qs 100 ml |

The following dyeing results were obtained

| | After dyeing | |
|---|---|---|
| | Dye [1] | Dye [2] |
| Bleached hair (SA40) | Bright yellow | Bright orange |
| Natural gray hair comprising 90% | Bright | Bright |
| white hairs | yellow | orange |
| Permanent-waved gray hair comprising 90% white hairs | Bright yellow | Bright orange |

Lightening of Th4 Keratin Fibers:

Lightening of the hair thus treated with dye 2 is observed: the locks of tone height 4 became visually lighter than untreated control locks.

Fastness with Respect to Successive Shampooing Operations:

The locks thus treated are divided into two; half are subjected to 5 successive shampooing operations according to a cycle which comprises wetting the locks with water, washing with shampooing operations (conventional shampoo), rinsing with water, followed by drying.

Visual Observations

During the shampooing operations, there is little visible bleeding of the color; the shampoo foam and the rinsing water are virtually uncolored.

The color observed on the locks is retained and the lightening effect remains visible on the hair of tone height 4 thus treated.

The invention claimed is:

1. A dye of formula (I):

$$A\text{-}(L)_p\text{-}C_{sat}\text{—}S\text{—}Y\text{-}(L')_{p'}\text{-}Y\text{—}S\text{—}C_{sat}\text{-}(L)_p\text{-}A \quad (I)$$

the organic or mineral acid salts, optical isomers and geometric isomers thereof, and the solvates such as hydrates:

in which formula (I):

A represents a radical containing at least one chromophore which is optionally cationic, colored, or colored and fluorescent;

L and L', which may be identical or different, represent:
a saturated or unsaturated, linear or branched $C_1$-$C_{20}$ hydrocarbon-based chain which is optionally substituted, optionally interrupted and/or optionally terminated at one or both of its ends with one or more divalent groups or combinations thereof chosen from —N(R)—, —O—, —S—, —C(O)— and —SO$_2$—, with R, R', which may be identical or different, being chosen from a hydrogen, and a $C_1$-$C_4$ alkyl, hydroxyalkyl and aminoalkyl radical; it being understood that said combination cannot form a disulfide bond —S—S—;

an arylene group,
a heteroarylene group,
a cycloalkylene group, or
a heterocycloalkylene group;

Y represents a carbonyl group or a heteroaryl group, which is cationic or noncationic, which comprises 5-13 members, which is optionally substituted, and which comprises from 1 to 5 heteroatoms chosen from oxygen, sulfur, or nitrogen atoms;

p and p', which may be identical or different, represent an integer equal to 0 or 1; and $C_{sat}$ represents an optionally substituted, linear or branched $C_1$-$C_{18}$ alkylene chain.

2. The dye of formula (I) as claimed in the preceding claim, in which the chromophore A represents:

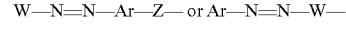

with:
W representing a heteroaryl, comprising a quaternary ammonium, optionally substituted preferably with one or more ($C_1$-$C_4$) alkyl groups;
Ar representing i) a 5- or 6-membered (hetero)aryl radical of phenyl or pyridium type, or ii) a (hetero) aromatic bicycle of naphthyl, benzopyridinyl, indolinyl or benzoindolinyl type, optionally substituted with one or more halogen atoms, with one or more alkyl groups, with one or more hydroxyl groups, with one or more alkoxy groups, with one or more hydroxyalkyl groups, with one or more amino or (di)alkylamino groups; and
Z representing an oxygen or sulfur atom, or a group NR' with R' representing a (hydroxy)($C_1$-$C_4$) alkyl group.

3. The dye of formula (I) as claimed in claim 1, in which chromophore A represents:

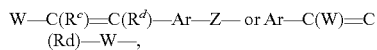

with:
W representing a heterocycle or a heteroaryl, comprising a quaternary ammonium;
Ar represents i) a 5- or 6-membered (hetero)aryl radical of phenyl or pyridinium type, or ii) a (hetero)aromatic bicycle of naphthyl, benzopyrydinium, indolinyl or benzoindolinyl type, optionally substituted with one or more halogen atoms, with one or more alkyl groups, with one or more hydroxyl groups; with one or more alkoxy groups, with one or more hydroxyalkyl groups, with one or more amino or (di)alkylamino groups, with one or more acylamino groups; with one or more heterocycloalkyl or heteroaryl groups comprising 5 or 6 members;
$R^c$, $R^d$, which may be identical or different, represent a hydrogen atom or a $C_1$-$C_4$ alkyl group;
Z representing an oxygen or sulfur atom, or a group NR' with R' representing a (hydroxy)($C_1$-$C_4$)alkyl group.

4. The dye of formula (I) as claimed in claim 1, in which Z is in the para_position on Ar relative to the azo function or of the double bond —C($R^c$)=C($R^d$)—.

5. The fluorescent dye of formula (I) as claimed in claim 1, such that Y represents a carbonyl group, L' represents a $C_2$-$C_6$ alkylene or arylene group, optionally interrupted with 1 or 2 heteroatoms and optionally terminated at each of its ends with a heteroatom, such as oxygen, or NR with R representing a hydrogen atom or a ($C_1$-$C_4$)alkyl group.

6. The dye of formula (I) as claimed in claim 1, chosen from the following dyes:

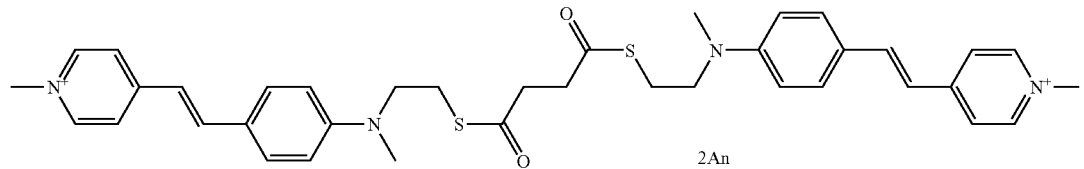
2An

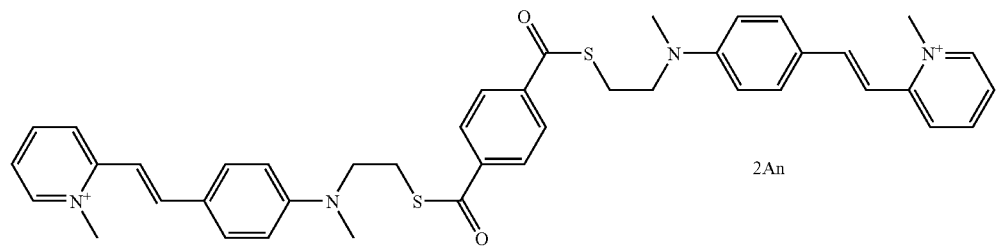
2An

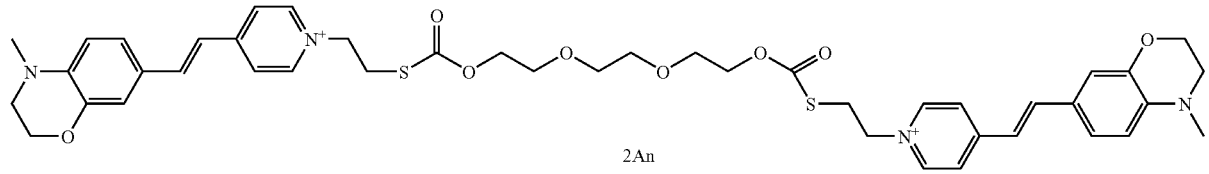
2An

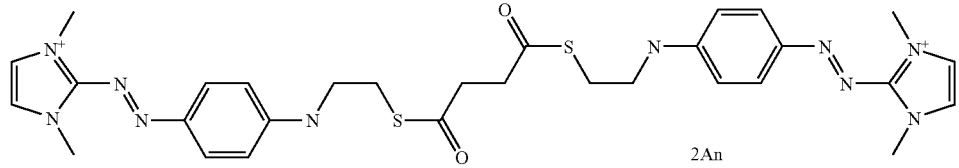
2An

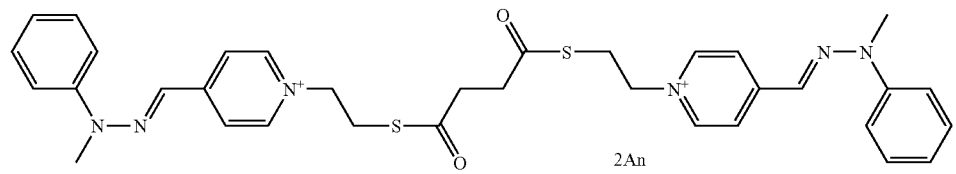
2An

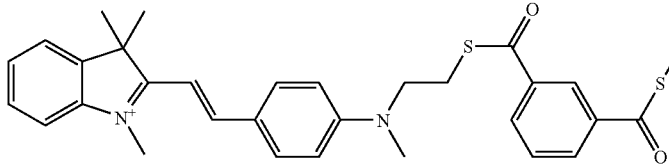
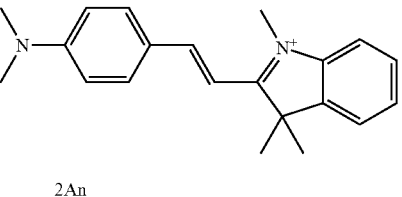

with An representing an anionic counterion.

7. A dye composition comprising, in a suitable cosmetic medium, a dye of formula (I) as defined in claim 1.

8. The dye composition as claimed in claim 7, comprising, in a suitable cosmetic medium:
   at least one dye of formula (I) as defined in claim 1;
   and at least one cosmetically acceptable basic agent.

9. A process for dyeing keratin materials, in which a suitable dye composition comprising at least one dye of formula (I) as claimed in claim 1 is applied to the materials.

10. The process for dyeing keratin materials as claimed in claim 9, wherein the keratin materials are dark keratin fibers having a tone height of less than or equal to 6.

11. The process as claimed in claim 9, in which the acidic or basic agent is applied after the application of the dye of formula (I) as defined in claim 1.

12. The process as claimed in claim 9, in which the composition comprises an oxidizing agent.

13. A multicompartment device in which a first compartment contains a dye composition comprising a dye of formula (I) as defined in claim 1, and a second compartment contains a basic agent.

14. A process for dyeing keratin materials, wherein the dye of formula (I) as defined in claim 1 is applied to the keratin materials.

15. A process for lightening dark keratin fibers, wherein the dye of formula (I) as claimed in claim 1 is applied to the dark keratin fibers.

16. The process of claim 14, wherein the keratin fibers are dark keratin fibers having a tone height of less than 6.

17. The process of claim 15, wherein the keratin fibers have a tone height of less than 6.

\* \* \* \* \*

UNITED STATES PATENT AND TRADEMARK OFFICE
CERTIFICATE OF CORRECTION

PATENT NO. : 8,075,638 B2
APPLICATION NO. : 12/679657
DATED : December 13, 2011
INVENTOR(S) : Greaves Page 1 of 1

It is certified that error appears in the above-identified patent and that said Letters Patent is hereby corrected as shown below:

Claim 3, col. 25, line 17, "or Ar-C(W)=C(Rd)-W-" should read
-- or Ar-C($R^c$)=C($R^d$)-W- --.

Claim 5, col. 26, line 17, "The fluorescent dye of" should read
-- The dye of --.

Signed and Sealed this
Twenty-eighth Day of February, 2012

David J. Kappos
*Director of the United States Patent and Trademark Office*